United States Patent [19]
Adams et al.

[11] Patent Number: 5,709,698
[45] Date of Patent: Jan. 20, 1998

[54] IRRIGATING/ASPIRATING SHAVER BLADE ASSEMBLY

[75] Inventors: Kenneth M. Adams, Tampa; Brian J. Fox, St. Petersburg; James Wallace, Holiday; Robert A. Van Wyk, Largo; Gary R. Heisler, Holiday; David Castagnetta, Clearwater; Cris Van Varsseveld, Oldsmar, all of Fla.

[73] Assignee: Linvatec Corporation, Largo, Fla.

[21] Appl. No.: 607,038

[22] Filed: Feb. 26, 1996

[51] Int. Cl.$^6$ .................................................. A61B 17/32
[52] U.S. Cl. ........................ 606/180; 606/167; 604/22
[58] Field of Search .................. 606/167, 170, 606/180, 177–179, 171; 604/22, 27, 28, 32, 35, 39, 43

[56] References Cited

U.S. PATENT DOCUMENTS

| | | | |
|---|---|---|---|
| 2,243,299 | 5/1941 | Travers | 604/39 |
| 2,257,369 | 9/1941 | Davis | 604/43 |
| 2,721,555 | 10/1955 | Jenney . | |
| 3,294,085 | 12/1966 | Wallace . | |
| 3,835,842 | 9/1974 | Iglesias . | |
| 3,844,272 | 10/1974 | Banko | 604/22 |
| 3,850,162 | 11/1974 | Iglesias . | |
| 3,850,175 | 11/1974 | Iglesias . | |
| 3,882,872 | 5/1975 | Douvas et al. . | |
| 3,900,022 | 8/1975 | Widran . | |
| 3,996,935 | 12/1976 | Banko | 604/22 |
| 4,167,943 | 9/1979 | Banko . | |
| 4,301,802 | 11/1981 | Poler . | |
| 4,517,977 | 5/1985 | Frost . | |
| 4,643,717 | 2/1987 | Cook et al. | 604/22 |
| 4,650,461 | 3/1987 | Woods | 604/28 |
| 4,650,463 | 3/1987 | LeVeen et al. | 604/43 |
| 4,674,502 | 6/1987 | Imonti . | |
| 4,715,848 | 12/1987 | Beroza | 604/35 |

(List continued on next page.)

FOREIGN PATENT DOCUMENTS

| | | |
|---|---|---|
| 0 240 457 | 3/1987 | European Pat. Off. . |
| 2 267 828 | 12/1993 | United Kingdom . |

OTHER PUBLICATIONS

Article Entitled "Stop Clogging in Your Sinus Cases—Put Our Typhoon Irrigated Cutter Blade in Your Handpiece", Trebay Medical Corp. 2 pages.

ENT Ear Nose & Throat Journal, "The Next Generation is Here—Introducing Hummer 2 ENT Micro Debrider", Jan. 1996 vol. 75 No.1, 2 pages.

*Primary Examiner*—Guy V. Tucker
*Assistant Examiner*—Patrick W. Rasche
*Attorney, Agent, or Firm*—Gene Warzecha

[57] ABSTRACT

A shaver blade assembly useable in either an irrigation-only mode, an aspiration-only mode or an irrigation/aspiration mode. The shaver blade assembly has a stationary elongated outer tube and a movable (e.g. rotatable) elongated inner tube, both inner and outer tubes having hubs attached to their proximal ends for attachment to a handpiece which provides power to move the inner blade relative to the outer blade. The inner and outer tubes are provided with cutting windows at their distal tips and the relative movement between these cutting windows acts to cut tissue during surgical procedures. The outer tube is provided with a fluid inlet port at the proximal end of its tubular surface and a fluid adapter is selectively attachable to the outer tube so as to provide a means for introducing irrigating fluid into the fluid port. The adapter is integrally formed with sealing surfaces which obviate the need for O-rings and the like. A longitudinally extending irrigating channel is provided between the inlet fluid port at one end of the irrigating channel and the outlet fluid port at the distal end of the irrigating channel by which fluid is communicated to the vicinity of the cutting windows when the shaver blade is used in the irrigation-only mode or the irrigation/ aspiration mode. The channel may be either the annular clearance space itself or a separate, dedicated groove or channel formed in the mating surfaces of the tubular members. Removing the adapter and the fluid supply enables the shaver to continue being used in an aspiration-only mode.

28 Claims, 10 Drawing Sheets

U.S. PATENT DOCUMENTS

| | | | |
|---|---|---|---|
| 4,750,488 | 6/1988 | Wuchinich et al. | 604/27 |
| 4,844,088 | 7/1989 | Kambin | 128/753 |
| 4,955,882 | 9/1990 | Hakky | 604/14 |
| 5,019,036 | 5/1991 | Stahl et al. | 604/22 |
| 5,163,433 | 11/1992 | Kagawa et al. | |
| 5,190,541 | 3/1993 | Abele et al. | 606/46 |
| 5,217,479 | 6/1993 | Shuler | 606/180 |
| 5,244,462 | 9/1993 | Delahuerga et al. | 606/42 |
| 5,300,069 | 4/1994 | Hunsberger et al. | 606/37 |
| 5,322,505 | 6/1994 | Krause et al. | 606/180 |
| 5,354,291 | 10/1994 | Bales et al. | 604/35 |
| 5,403,276 | 4/1995 | Schechter et al. | 604/22 |
| 5,403,317 | 4/1995 | Bonutti | 606/80 |
| 5,405,348 | 4/1995 | Anspach, Jr. et al. | 606/80 |
| 5,505,210 | 4/1996 | Clement | 128/753 |

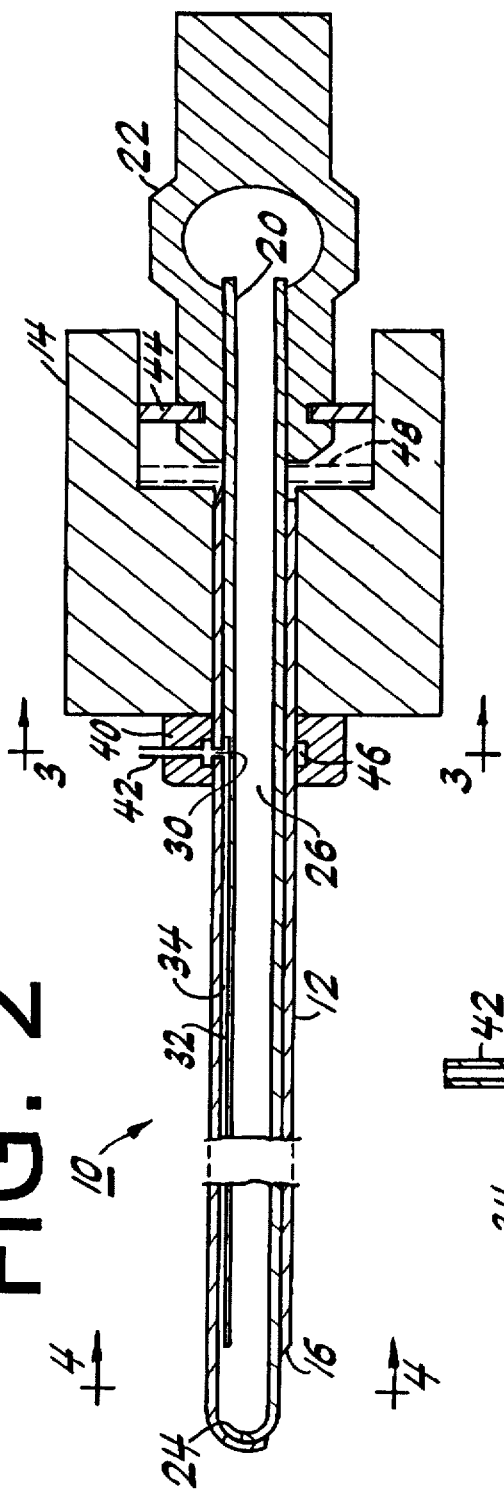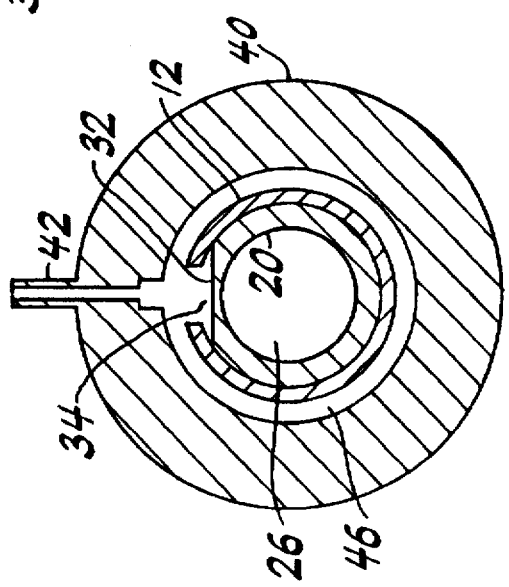

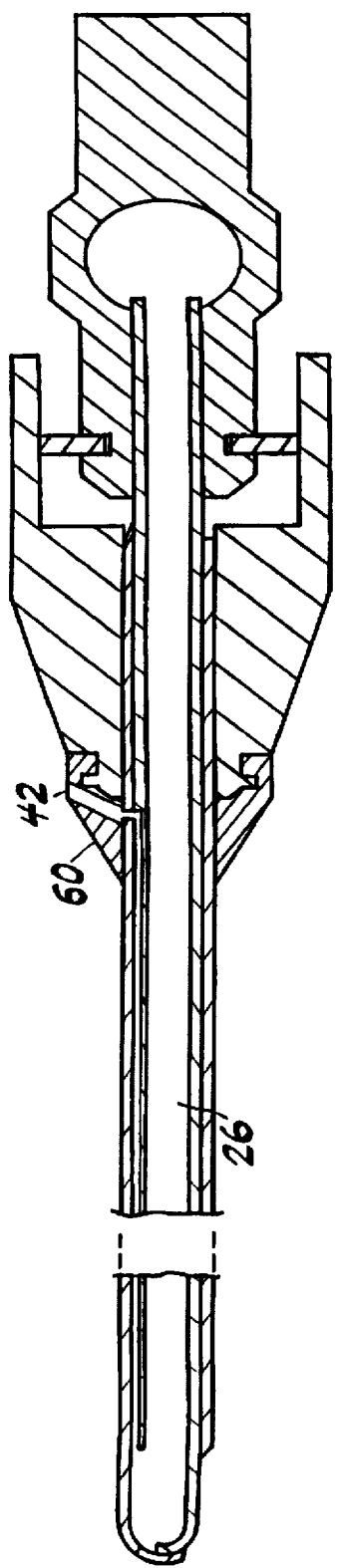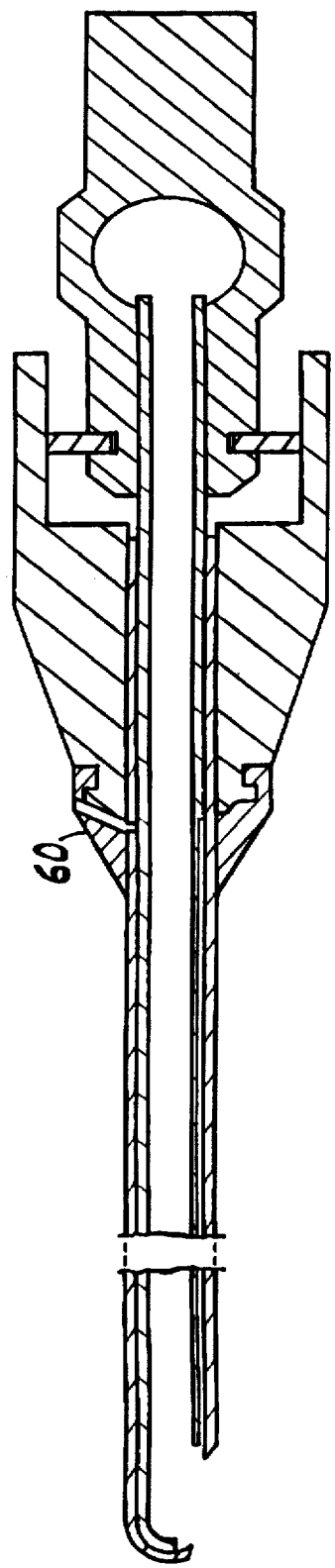

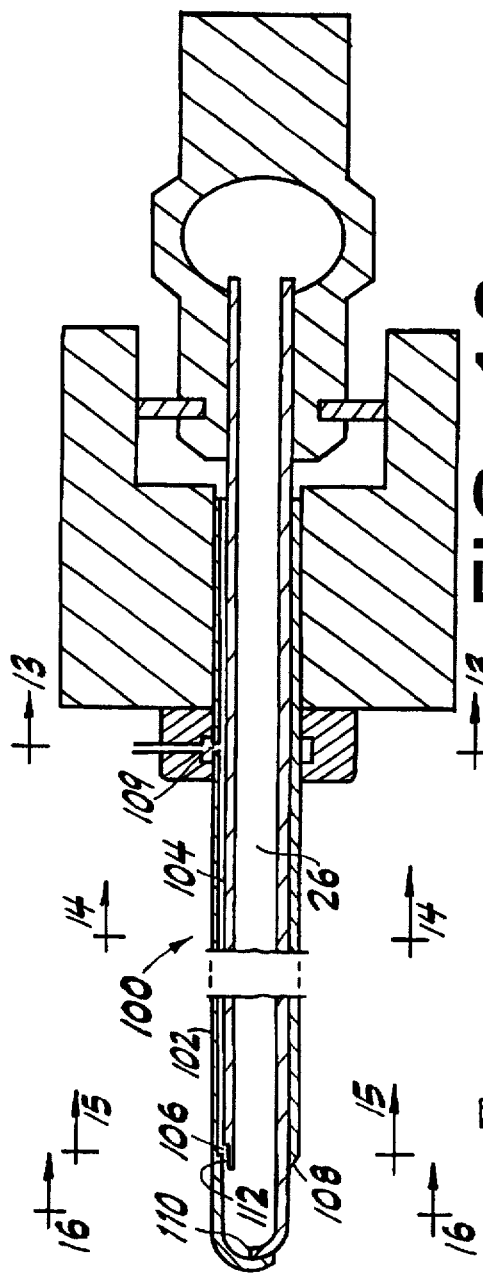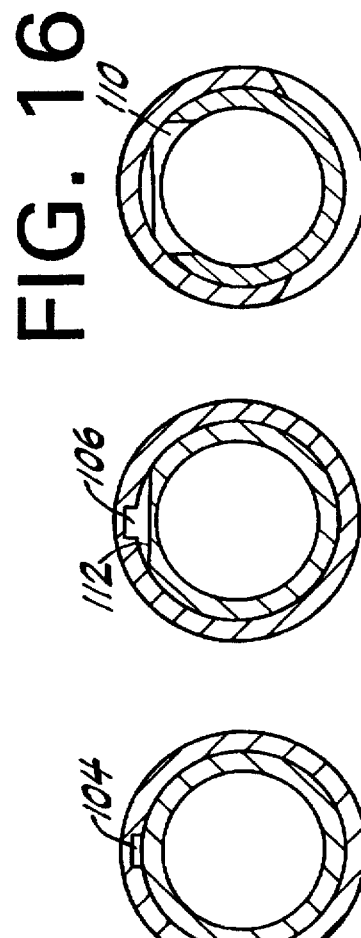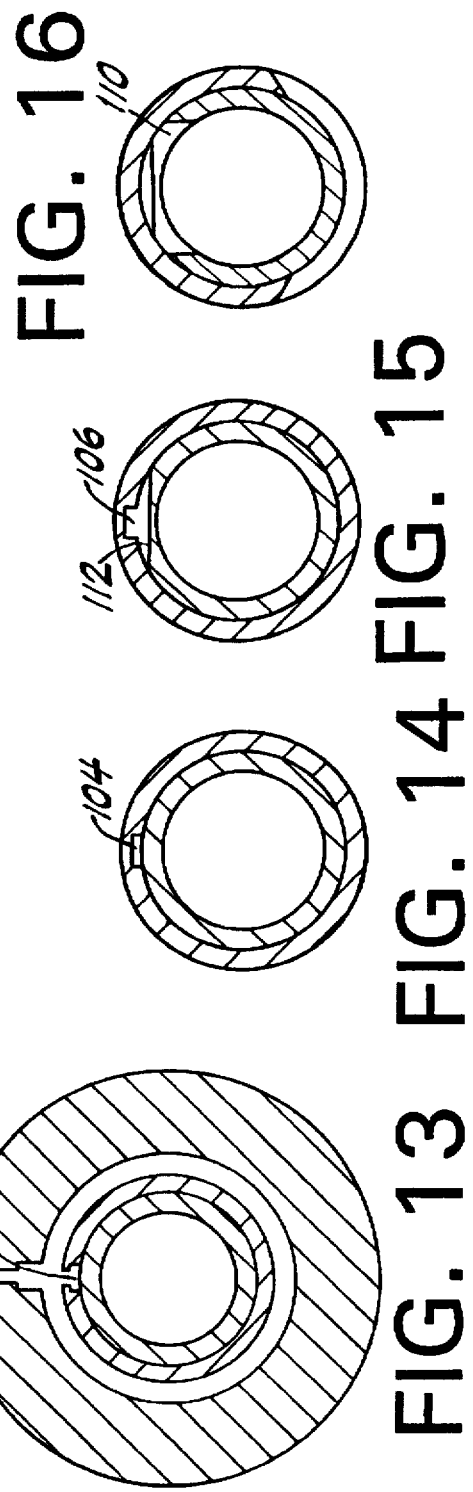

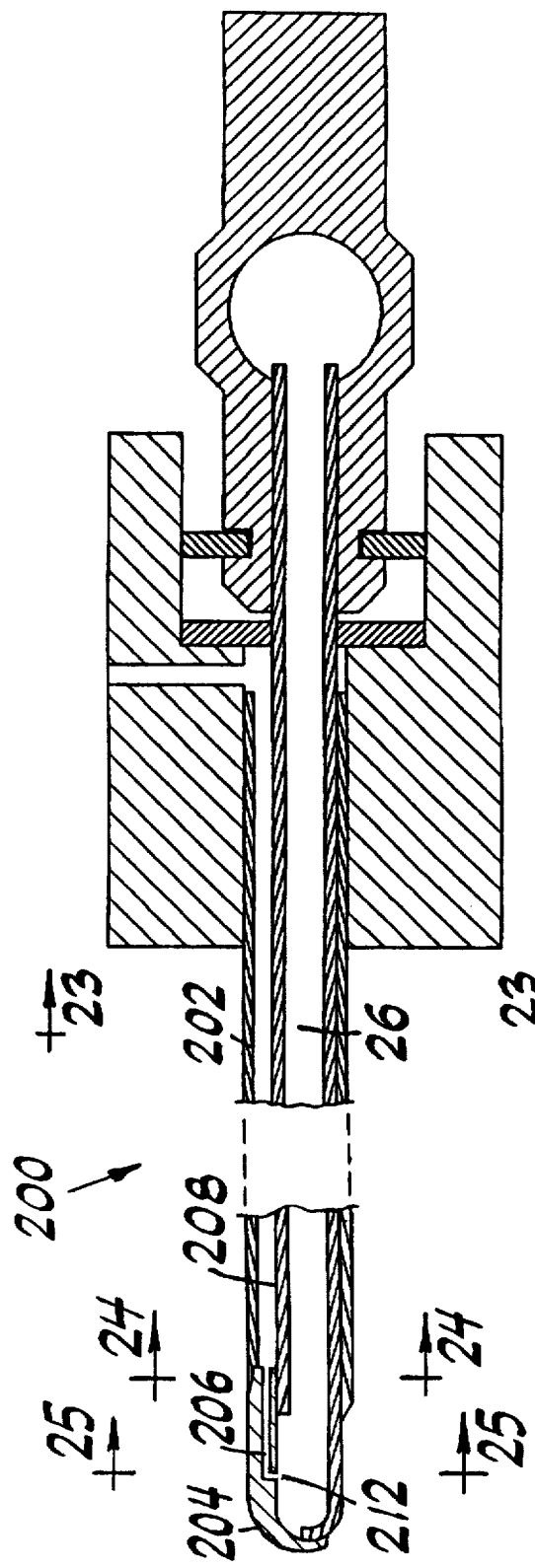
FIG. 22
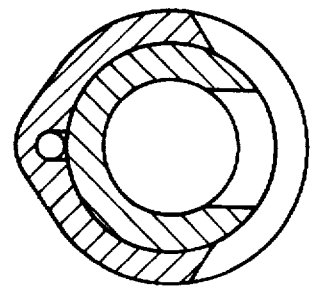
FIG. 26
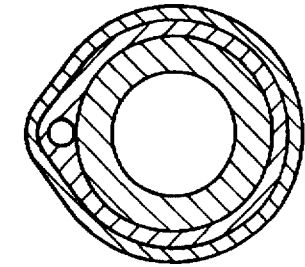
FIG. 25
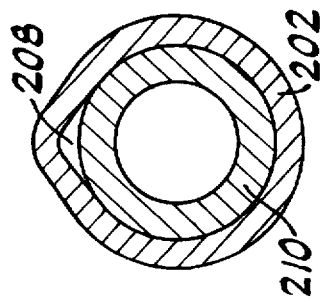
FIG. 24
FIG. 23

IRRIGATING/ASPIRATING SHAVER BLADE ASSEMBLY

BACKGROUND OF THE INVENTION

1. Field of the Invention

The invention relates generally to powered endoscopic cutting devices. More particularly, the invention relates to rotating shaver blades for use in various endoscopic surgical procedures.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments and scopes used in the surgical procedure must be elongated to permit the distal ends of the instruments and cameras to reach the surgical site. Some conventional surgical cutting instruments (shavers) for use in closed surgery are rotary powered and have a straight, elongated outer tubular member and a straight, elongated inner tubular member concentrically disposed in the outer tubular member. The inner and outer members both separately and jointly are sometimes referred to in the art as "blades" and are usually disposable. The outer member has a distal end having an opening in the end or side wall (or both) to form a cutting port or window and the inner member has a distal end disposed adjacent the opening in the distal end of the outer member. The inner member is (usually) easily insertable into and removable from the outer member to facilitate cleaning or interchanging parts. Each of the elongated members has a hub or termination at its proximal end in order to attach the components to a rotary drive means within a reusable handpiece. The distal end of the inner tubular member has a cutting means or cutting edge for engaging tissue via the opening in the distal end of the outer tubular member. In many cases (but not all) this distal cutting means cooperates with the opening in the outer member to shear, cut or trim tissue. In some cases, such as abrading burrs, the opening in the outer member merely allows access to the tissue and does not otherwise cooperate with the cutting means. The term "cutting edge" or "cutting means" as used herein is intended to include abrading (e.g. burrs) and other devices whether or not there is any traditional cutting or shaving action and whether or not there is any cooperative shearing action. The inner tubular member is rotatably driven about its axis from its proximal end, normally via a handpiece having a small electric motor which is controlled by either finger actuated switches on the handpiece, a foot switch or switches on a console supplying power to the handpiece. The distal end of the various styles of inner tubular members can have various configurations depending upon the surgical procedure to be performed, and the opening in the distal end of the outer tubular member would then have a configuration adapted to cooperate with the particular configuration of the distal end on the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generically as cutting means.

The aforementioned elongated surgical cutting instruments have also been produced in angled configurations in which the axes of the distal tips of the inner and outer members are aligned and offset or bent at a fixed angle relative to the axes of the proximal ends of the aligned inner and outer members. Examples of such fixed-angle, rotary surgical instruments are shown in U.S. Pat. No. 4,646,738 (Trott), assigned to the assignee hereof, and in European Patent Application 0 445 918 (Krause et al.). In other respects the operation of these fixed-angle shavers is largely the same as that of the straight shavers described above. Known fixed-angle shavers are generally produced with only one degree of bend —usually 15°. Recently a variable-angle (i.e. bendable) rotary shaver system has been introduced and is described in U.S. Pat. No. 5,411,514 (Fucci et al.), assigned to the assignee hereof, in which the outer tube may be bent by a user to a user-selected angle while still enabling the inner tube to be selectively inserted into and removed from the outer tube. The inner member of this device has a hollow plastic body, such as polyaryletherketone, and a metallic distal tip into which a cutting edge is formed. In all of these devices, the loose tissue resulting from the cutting, resecting or abrading procedure may be aspirated through the hollow lumen of the inner tubular member to be collected via a vacuum tube communicating with the handpiece. The devices are generally used in an aspiration-only mode since the surgical site is usually distended by some fluid medium.

However, during certain surgical procedures there is no fluid medium surrounding the work site and it is desirable to introduce irrigating fluid to the surgical site in order to simply irrigate the site to improve visualization or to facilitate the aspiration of debris. Such irrigation is usually provided by separate instruments generally known as irrigation/aspiration devices which can be used to either irrigate or aspirate a site. Recently, powered endoscopic surgical cutting devices have been produced in order to simultaneously provide irrigation and aspiration without the necessity of using a separate instrument.

One known device is produced by TreBay Medical Corporation of Clearwater, Fla. and comprises a rotating shaver blade having a separate fluid tube secured to the outside of the outer tubular member. The proximal end of the tube is connected to a source of fluid supply and the distal end of the tube is joined to a fluid port formed in the distal end of the outer tubular member. Fluid is cyclically permitted to flow into the inner tubular member when the inner cutting window faces the fluid port.

Another known irrigating shaver blade assembly is the Wizard produced by Xomed-Treace Inc. of Jacksonville, Fla. This device utilizes a dual-lumen plug to connect a rotating shaver blade to a fluid source. One lumen of the plug permits fluid to flow into the space between the inner and outer tubular members and the other lumen permits aspiration through the lumen of the inner member.

The prior art irrigating shavers are dedicated for use in an irrigating/aspirating mode. That is, special blade assemblies are produced to enable the use of the shaver in an irrigating/aspirating mode in which fluid is passed to the surgical site and debris and fluid are aspirated from the site. It would be desirable to have a single, multi-purpose shaver blade assembly which could be used in either a non-irrigating or aspiration-only mode, in an irrigating-only mode or in an irrigating/aspirating mode.

It is accordingly an object of this invention to produce a rotating shaver blade capable of being used in either a non-irrigating or aspiration-only mode, in an irrigating-only mode or in an irrigating/aspirating mode.

It is another object of this invention to produce a powered shaver system having a shaver blade assembly useable in either an aspiration-only mode, an irrigation-only mode or an irrigation/aspiration mode.

It is yet another object of this invention to produce such a powered shaver system suitable for fixed and bendable shavers and suitable for use with gravity-fed or pumped fluid sources.

It is also an object of this invention to produce such a powered shaver system while minimizing the diameter of the elongated shaver assembly.

SUMMARY OF THE INVENTION

These and other objects of this invention are achieved by the preferred embodiment disclosed herein which is a shaver blade assembly for irrigating, aspirating or irrigating and aspirating a surgical site. The assembly comprises an elongated outer tubular member having a distal end, a proximal end, a cutting opening at the distal end, a hub at the proximal end, and an irrigating fluid port in the surface of the outer tubular member. The fluid port is intermediate the distal and proximal ends. An elongated inner tubular member is adapted to move within the outer tubular member and has a distal end, proximal end, a cutting window at the distal end, and a hub at the proximal end. An elongated channel is provided between the irrigating fluid port and the cutting window, the channel being defined by the inner surface of the outer member and the outer surface of the inner member. A fluid adapter means is provided for connecting the irrigating fluid port to a source of irrigating fluid. Selectively directing fluid through the assembly enables the device to be used in either a non-irrigating or aspiration-only mode (with fluid turned off and suction turned on), in an irrigating-only mode (with fluid turned on and suction turned off) or in an irrigating/aspirating mode (with both fluid and suction turned on).

In another aspect the invention is a method of adapting a shaver blade assembly to be used in a non-irrigating or aspiration-only mode, in an irrigating-only mode or in an irrigating/aspirating mode. The shaver blade assembly has an elongated inner tubular member movable within an elongated outer tubular member and the method comprises the steps of forming a fluid inlet port in the wall of the outer tubular member, providing a fluid adapter to connect the port to a source of fluid when operation in an irrigating-only mode or in an irrigating/aspirating mode. Selectively turning fluid and suction on in various combinations enables one blade assembly to be used in a variety of modes.

BRIEF DESCRIPTION OF THE DRAWINGS

FIG. 2 is a diagrammatic, assembled side elevational view of FIG. 1 in cross-section, deleting the handpiece.

FIG. 3 is a sectional view of FIG. 2 along the lines 3—3.

FIG. 4 is a sectional view of FIG. 2 along the lines 4—4.

FIG. 8 is an alternate embodiment of the invention.

FIG. 9 is a view of FIG. 8 with the inner member being in a diametrically opposed position.

FIG. 12 is another alternate embodiment of the invention.

FIG. 13 is a sectional view of FIG. 12 taken along the lines 13—13.

FIG. 14 is a sectional view of FIG. 12 taken along the lines 14—14.

FIG. 15 is a sectional view of FIG. 12 taken along the lines 15—15.

FIG. 16 is a sectional view of FIG. 12 taken along the lines 16—16.

FIG. 22 is another alternate embodiment of the invention.

FIG. 23 is a sectional view of FIG. 22 taken along the lines 23—23.

FIG. 24 is a sectional view of FIG. 22 taken along the lines 24—24.

FIG. 25 is a sectional view of FIG. 21 taken along the lines 25—25.

FIG. 26 is a view of FIG. 25 showing the inner blade in a diametrically opposed position.

DESCRIPTION OF THE PREFERRED EMBODIMENT

Figure 1:
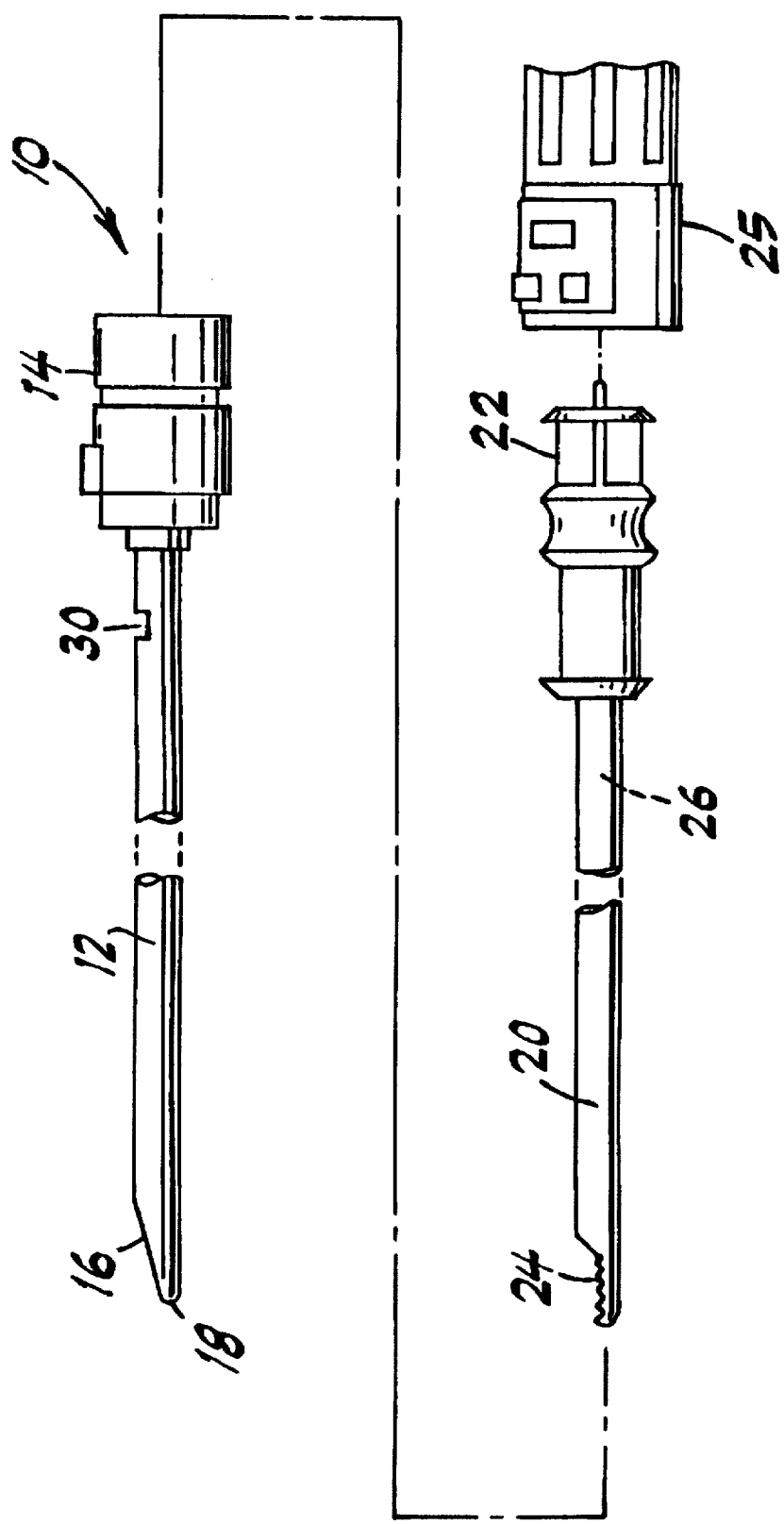
FIG. 1 is an exploded side elevational view of a shaver blade assembly constructed in accordance with the principles of this invention.
Figure 5:
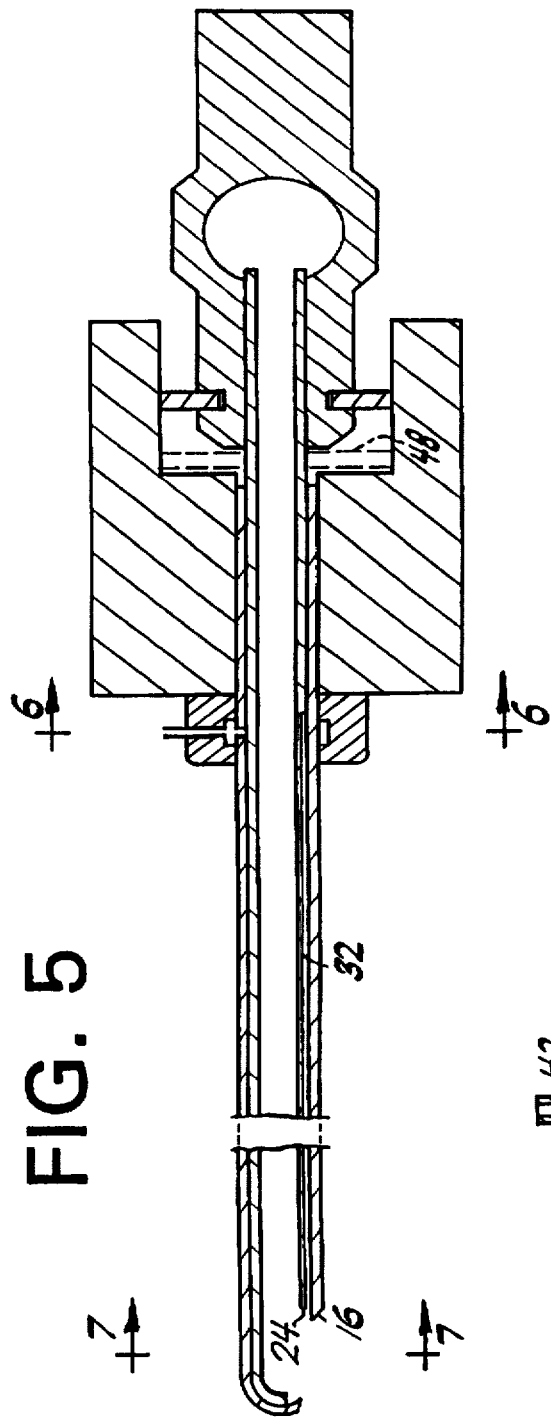
FIG. 5 is a view of FIG. 2 showing the inner tubular member of the assembly in a position diametrically opposed from that shown in FIG. 2.
Figure 7:
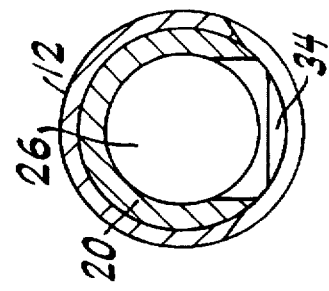
FIG. 7 is a sectional view of FIG. 5 taken along the lines 7—7.
Figure 6:
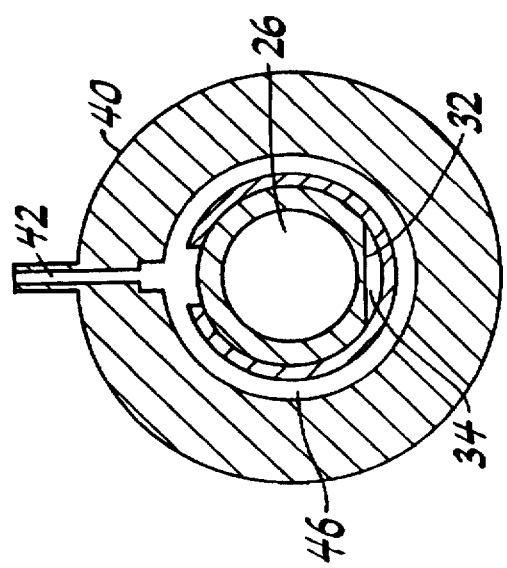
FIG. 6 is a sectional view of FIG. 5 taken along the lines 6—6.

One embodiment of the invention is shown in FIGS. 1–7 showing an existing shaver blade assembly, originally produced for use in an aspiration-only mode, modified for use in an irrigation-only mode or an irrigation/aspiration mode and referred to as assembly 10. Shaver blade assembly 10 comprises a stationary outer tube 12, having a hub 14 at its proximal end and a cutting opening 16 at its distal end, a rotatable inner tube 20 having an inner hub 22 at its proximal end and a cutting tip 24 at its proximal end. The assembly 10 is designed to fit in a conventional handpiece 25 which provides power to the inner member and which communicates suction to the lumen 26 in the aspirating modes.

In the preferred embodiment, an existing shaver blade is modified by machining an irrigation supply port 30 in the side of the proximal end of the outer tube diametrically opposite cutting opening 16. The annular clearance between the inner and outer tube is usually sufficient to act as the irrigating channel and provide adequate fluid flow to the distal end of the shaver blade. For example, an inner member having an OD of 0.140 inches and an outer member having an ID of 0.145 inches will produce an irrigating channel in the form of an annular clearance space having a 0.005 inch radial thickness. In certain cases if this is insufficient, a flat 32 may be formed on the inner tube outside surface as shown in FIGS. 2–7 (not to scale) so as to produce an irrigation channel 34 between the inner and outer tubes. The flat 32 on the inner tube is aligned with the inner tube cutting window 24 and extends from the window proximally a distance sufficient to allow flow from the irrigation supply port 30 into the irrigation channel when port 30 and channel 34 are angularly aligned (best seen in FIGS. 2 and 3). A removable, annular adapter 40 having a port 42 is attachable to outer tube 12 to communicate fluid via a tube from a fluid supply (not shown) to port 30. The fluid supply may be pumped or gravity-fed, depending upon the size of the irrigating channel. The adapter should be sized to slide onto the outer member and to stay in place (if not locked in place as discussed below). Preferably, the adapter is disposable.

A seal 44 is interposed between the inner and outer hubs 22 and 14 as shown in FIGS. 2–7 or optionally as seal 48 between the outer hub 14 and inner tube 20 (shown in phantom) in order to prevent leakage in a proximal direction. Additionally, one or more seals could be placed in the adapter if necessary to prevent leakage between it and the outer member.

In the case where the annular clearance space serves as the channel, a lubricant such as food grade grease may enhance fluid flow. Consequently, if the shaver blade manufacturing process normally incorporates such lubricant, it need not be changed.

Figure 10:
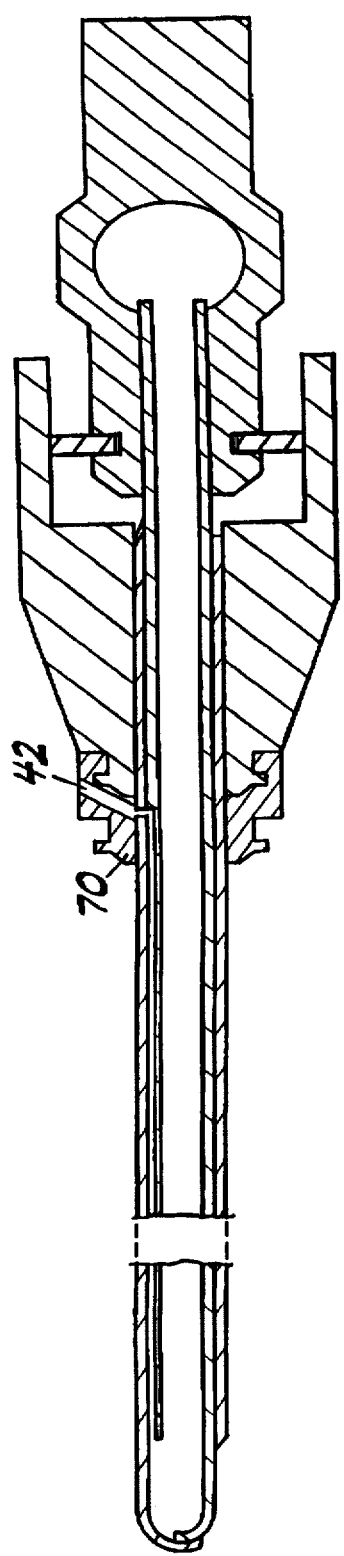
FIG. 10 is another alternate embodiment of the invention.
Figure 11:
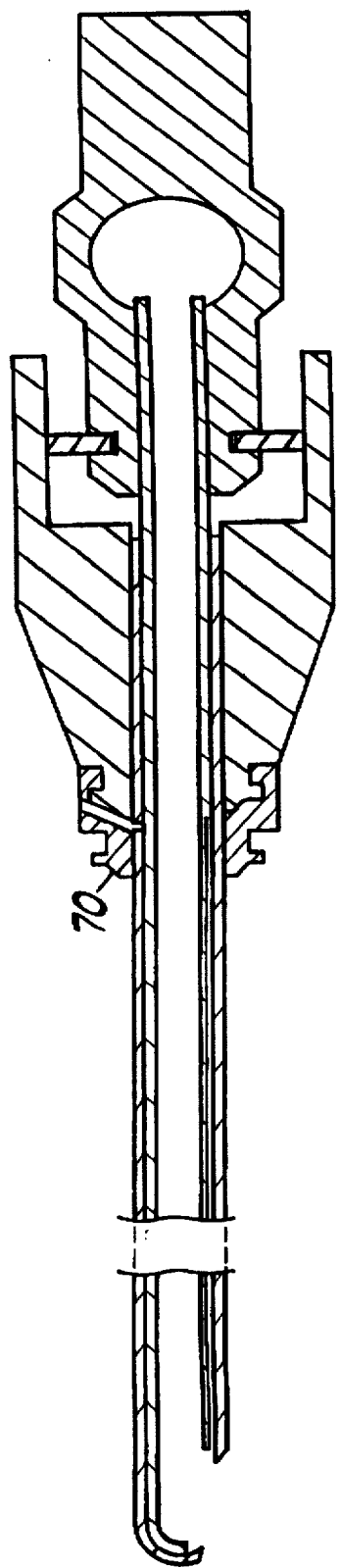
FIG. 11 is a view of FIG. 10 showing the inner member in a diametrically opposed position.
Figure 18:
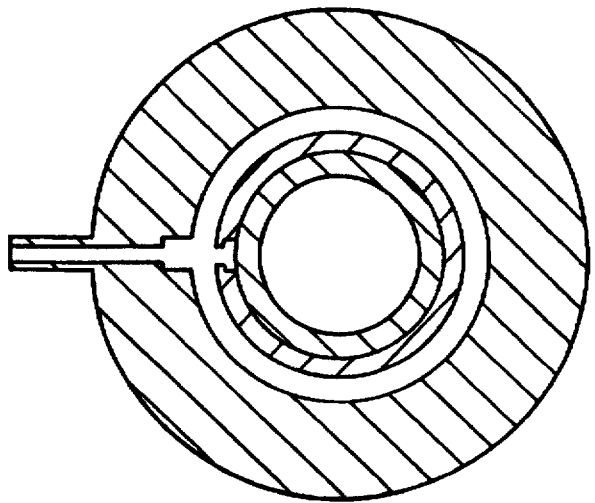
FIG. 18 is a sectional view of FIG. 17 taken along the lines 18—18.

In the embodiment of FIG. 2 liquid is supplied from the annular adapter 40 to fluid port 30 by means of an annular channel 46 formed by a recess in the adapter adjacent the outer tube, thereby making angular alignment of the supply port 30 and the adapter inlet port 42 unnecessary. In other embodiments shown in FIGS. 8–11, the adapter is affixed to the outer hub by means of some locking mechanism. The embodiments are identical to that of FIGS. 2–7 except that the adapters are different. In the embodiment of FIGS. 8 and 9 the adapter 60 has an inclined inlet port and is formed with a Luer lock configuration at its distal end and a bayonet or cannula lock at its proximal end. In the embodiment of FIGS. 9 and 10, the adapter 70 may have male and female bayonet lock at opposite ends. These configurations enable the adapter ring to be used with standard cannulas in the same manner as an unaltered shaver blade assembly. Fixation in this manner automatically establishes the angular orientation of the adapter inlet 42 with the fluid port 30 so as to make the adapter channel 46 unnecessary.

The embodiments described above may be used in either an aspiration-only mode in which no irrigating fluid is supplied or in an irrigation-only mode or an irrigation/ aspiration mode. In the latter two modes, the adapter inlet port 42 is connected to a fluid supply source which may be pressurized or simply gravity-fed and the fluid flow is turned on (via a valve, for example, not shown). Suction or aspiration is supplied to the inner tube lumen 26 by means of the inner hub aspiration port in a conventional manner. In the irrigation-only mode, the suction is off while the irrigation is on and the cutting window held open. In the irrigation/ aspiration mode, both irrigation and suction are on. The flow of liquid through the irrigation channel 34 is due to pressure provided by the fluid supply and suction supplied by the aspiration port. Flow is not continuous but rather pulsed due to the "valving" action of the irrigation port and the irrigation channel.

While the "valving" action may be implemented as a function of whether the channel or port is open or closed, in the preferred embodiment the "valving" action is implemented so as to cyclically increase suction on the fluid flow, thereby producing a fluid "pulsing" effect. It is this effect which enables use of the seemingly small annular clearance space as the irrigating channel. That is, when the cutting window is closed as in FIGS. 2, 8, 10, 12 and 22, all of the suction through lumen 26 is directed against fluid flowing in the channel. This is true whether the channel is the annular clearance space or a discrete channel 34. In all embodiments, when the cutting window is in the open position as shown in FIGS. 5, 9, 11 and 17 relatively low flow will occur only through the annular clearance space between the inner and outer tubes. As the inner tube is rotated so as to close the cutting window, suction increases, channel 34 intersects the irrigation port 30 and increased flow commences. Such flow will continue until the irrigation channel is rotated past the irrigation port. The amount of flow is determined by (1) the size of the irrigation channel, (2) the size and shape of the irrigation port; (3) pressure of the water supply and (4) the level of vacuum applied to the aspiration port.

Figure 17:
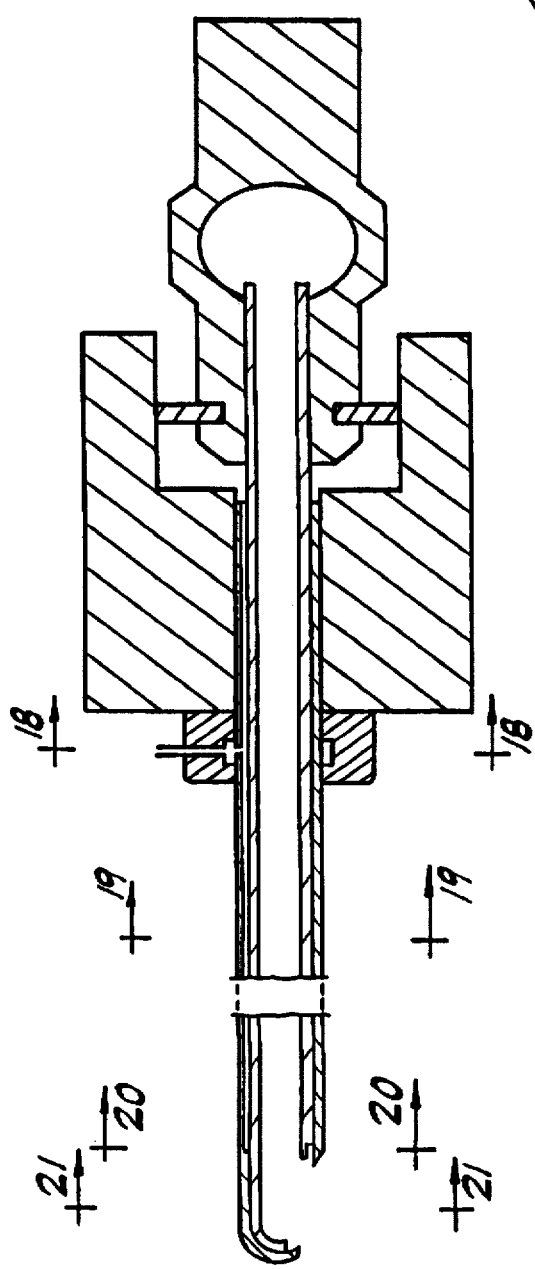
FIG. 17 is a view of FIG. 12 showing the inner member in a diametrically opposed position.
Figure 21:
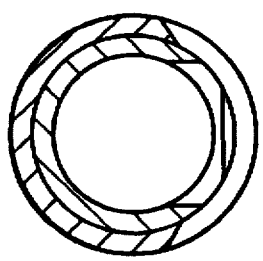
FIG. 21 is a sectional view of FIG. 17 taken along the lines 21—21.
Figure 20:
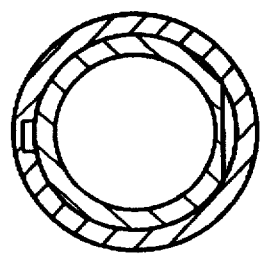
FIG. 20 is a sectional view of FIG. 17 taken along the lines 20—20.
Figure 19:
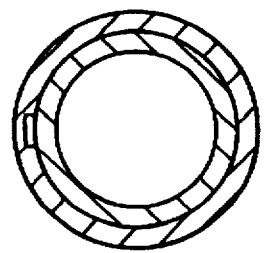
FIG. 19 is a sectional view of FIG. 17 taken along the lines 19—19.

While the preceding embodiments may be manufactured with a variety of materials and combinations (e.g. both inner and outer tubes of metal; inner tube of polymeric material and outer tube of metal; both inner and outer tubes of polymeric material, etc.), in certain instances (as in the case of non-metallic inner tubes) it may be undesirable to have an irrigation channel formed by an elongated recess on the inner tube. In such instances, an alternative embodiment may be produced in which the irrigation channel is produced in the inner surface of the outer tube as shown in FIGS. 12–21 or is produced in a space between a non-cylindrical "tear drop shaped" outer tube and a cylindrical inner tube as shown in FIGS. 22–26. In the former case with the channel in the inner surface of the outer tube, shaver blade assembly 100 has an outer tube 102 which has formed therein an irrigation channel 104 in fixed alignment with the distal irrigation port 106 on the surface of the tube radially opposite the outer tube cutting window 108. As before, flow of fluid into the handpiece is prevented by a seal between the inner and outer hubs or between the inner tube and outer hub. The irrigation channel 104 extends axially from the proximal end of the tube, past fluid inlet port 109 to a point slightly proximal to the inner tube cutting window 110. A flat 112 is machined on the outer surface of the distal end of the inner tube, angularly aligned with the cutting window 110, and extends proximally from the window to a point proximal to the distal end of channel 104. This creates an overlap of flat 112 and channels 104 which acts to communicate fluid from channel 104 to the interior of the inner blade to cyclically permit fluid flow when the flat 112 and irrigation channel 104 are in angular alignment (as shown in FIGS. 15 and 16). Interaction of the inner tube flat 112 with the outer tube irrigation channel 104 produces a valving action permitting only very little fluid flow, if any, when the cutting window is in the open position as shown in FIGS. 17, 20 and 21.

In the case of shaver blade assembly 200 having the "tear drop" outer tube 202 shown in FIG. 22, a distal "shell" 204 containing an irrigation fluid channel 206 is bonded to the outer tube end by laser welding or another suitable method. The irrigation channel 208 between the outer and inner tubes 202 and 210 conducts fluid to the shell irrigation channel 206 from which it is introduced into the cutting area through a port 212 in the inner surface of the shell opposite the cutting window. Valving action is produced by the interaction of the inner tube outer surface and the irrigation port 212. Only seepage can occur when the cutting windows of the inner and outer tubes are aligned.

Figure 27:
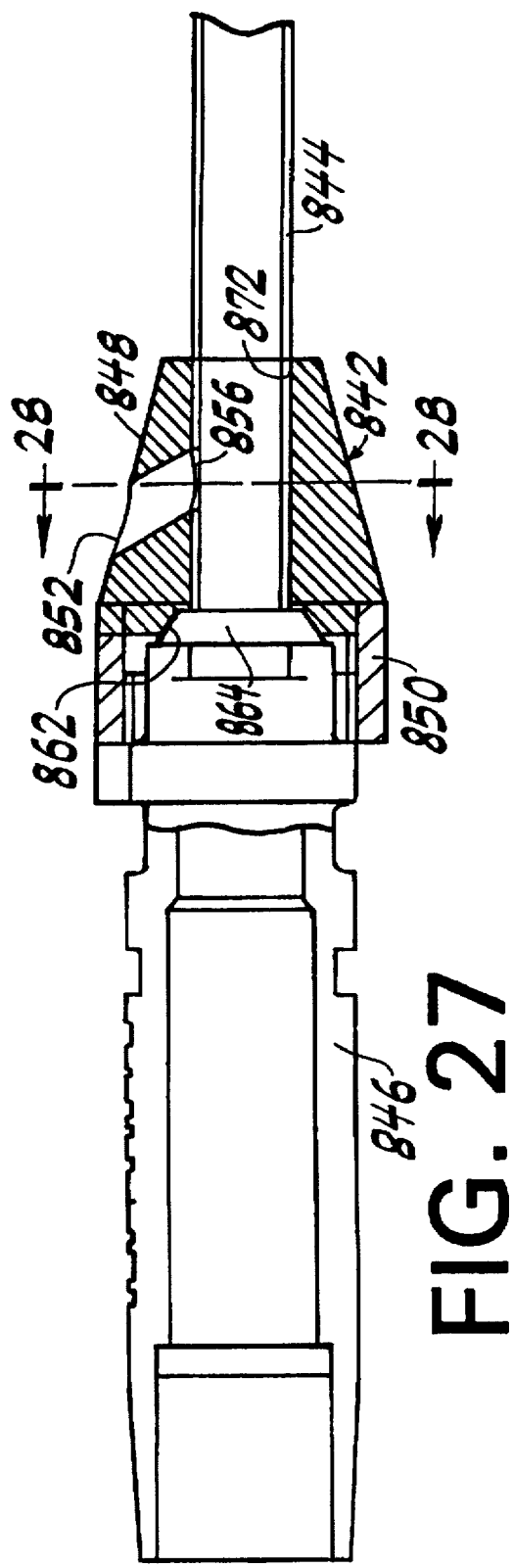
FIG. 27 is a side elevation view, partially in cross-section of the proximal end of the outer member of a shaver blade assembly combined with a fluid adapter constructed in accordance with the principles of this invention.
Figure 28:
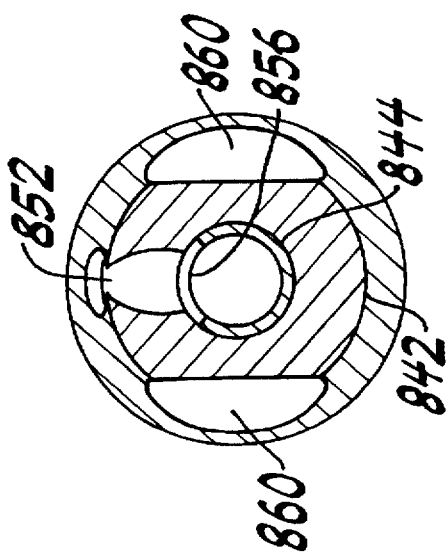
FIG. 28 is a cross-sectional view of FIG. 27 taken along the lines 28—28.

A more detailed view of adapter 60 is shown in FIGS. 27-31 as adapter 842. The adapter comprises a distal portion 848 and a proximal portion 850 securely joined together although it will be understood that adapter 842 could be formed in one integral piece. In the preferred embodiment, distal portion 848 is a frustoconical portion having an inner cylindrical surface 872 adapted to receive the outer surface of outer tubular member 844. The proximal portion 850 is adapted to engage the distal end of hub 846 in such a way as to not only securely attach the adapter to the hub but to align port 852 with fluid irrigation port 856 formed in the wall of the outer tubular member 844. As best seen in FIG. 28, adapter 842 is sized to snugly engage the outer surface of elongated tubular member 844 and further includes a pair of opposed indentations 860 which help to manipulate the adapter in use. It will be noted in FIG. 28 that the arcuate length of fluid port 856 is somewhat greater than the adjacent arcuate length of port 852 in order to provide some tolerance in the keying arrangement by which the adapter is secured to the hub.

Figure 29:
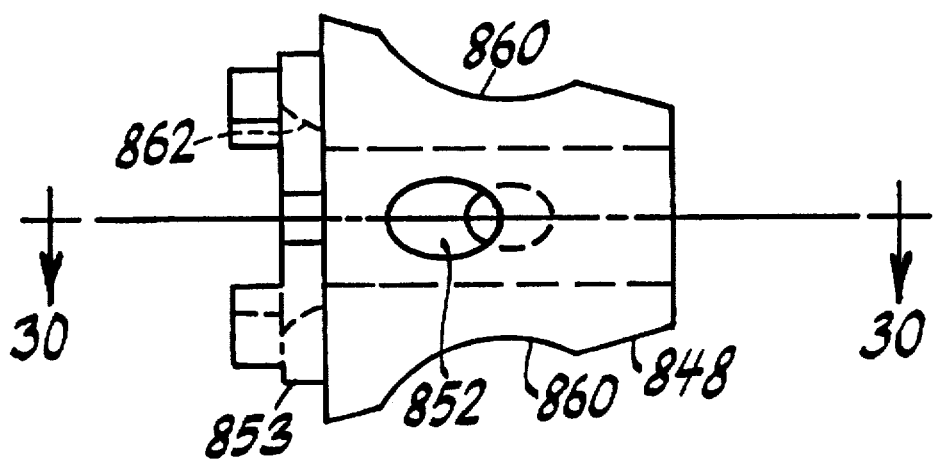
FIG. 29 is a top plan view of the frusto-conical, proximal portion of the adapter shown in FIG. 27.

A top plan view of the front portion 848 of the adapter is shown in FIG. 29 in which the opposed indentations 860 are more clearly visible. The proximal end of front portion 842 is provided with arcuately and longitudinally extending projections 853 in order to mate with cylindrical portion 850 in a manner which will be understood by those skilled in the art.

Figure 30:
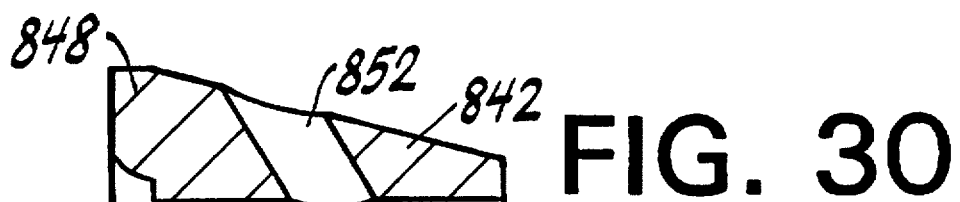
FIG. 30 is a cross-sectional view of FIG. 29 taken along the lines 30—30.
Figure 31:
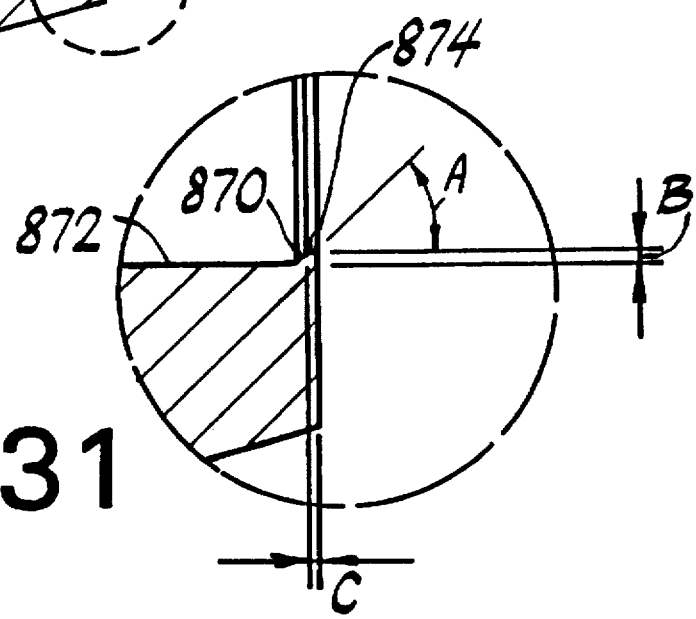
FIG. 31 is an exploded view of a proximal portion of the adapter shown in FIG. 30.

As best seen in FIG. 30, adapter 842 is provided with a pair of integrally formed seal elements in order to engage the outer tubular member of the shaver blade assembly in a fluid tight manner. Thus, a seal is provided between the adapter and the outer tubular member on both the proximal and distal sides of port 852. The distal seal is provided at the distal end of frustoconical portion 842 by an annular lip 870. As best seen in the enlarged FIG. 31, lip 870 extends radially inwardly a predetermined distance from surface 872 at a predetermined angle A which is, in the preferred embodiment, on the order of 45°. It will be understood that this angle may vary depending upon other design considerations. The radially inward-most end of lip 870 is provided with a flat annular surface 874 extending longitudinally a predetermined amount C and disposed radially inwardly of surface 872 by a predetermined amount B. In the preferred embodiment, adapter 842 is formed of Lexan and dimensions B and C are 0.003 inches and 0.006 inches, respectively, with the diameter of cylindrical surface 872 being on the order of 0.165 inches.

The proximal sealing function is achieved by an annular surface 862 situated at the proximal end of frustoconical portion 842. Surface 862 has a predetermined radius of curvature which may in certain embodiments be on the order of 0.092 inches. As best seen in FIG. 27, the proximal seal between adapter 842 and hub 846 is achieved by the interaction between surface 862 and a frustoconical extension 864 formed at the proximal end of hub 846. The keying arrangement (not shown) by which adapter 842 is secured to hub 846 serves not only to align the ports as mentioned above but also to squeeze surfaces 862 and 864 together. Thus, a fluid tight arrangement is achieved both proximally and distally of fluid port 856 without the necessity of auxiliary sealing devices such as O-rings and the like.

While the preferred embodiment has been described in the context of a rotary blade, the invention is equally suitable for burrs as well. Additionally, the invention could be easily adapted to reciprocating surgical cutters in which a tubular inner member longitudinally reciprocates within a tubular outer member. The cutting action in such devices occurs as the distal cutting edges of the inner and outer members interact.

It will be understood by those skilled in the art that numerous improvements and modifications may be made to the preferred embodiment of the invention disclosed herein without departing from the spirit and scope thereof.

What is claimed is:

1. A shaver blade assembly for resecting tissue from a surgical site while being connected to a source of fluid and a source of aspiration such that tissue at the surgical site may be selectively subjected to irrigating, aspirating or irrigating and aspirating a surgical site at the same time comprising:

an elongated outer tubular member having a distal end, a proximal end, a cutting opening at said distal end, a hub at said proximal end, and an irrigating fluid inflow port in said outer tubular member intermediate said distal and proximal ends;

an elongated inner tubular member adapted to move relative to said outer tubular member and having a distal end, proximal end, a cutting window at said distal end, and a hub at said proximal end;

an elongated channel between said irrigating fluid inflow port and said cutting window, said channel defined by the inner surface of said outer member and the outer surface of said inner member; and a fluid adapter means selectively attachable to said outer tubular member adjacent said irrigating fluid inflow port for connecting said irrigating fluid port to said source of fluid.

2. A shaver blade assembly according to claim 1 further comprising a fluid seal between the proximal ends of said inner and outer tubular members.

3. A shaver blade assembly according to claim 1 wherein said elongated channel comprises an annular cylindrical clearance space between said inner and outer tubular members.

4. A shaver blade assembly according to claim 3 wherein said cutting opening at said distal end of said outer tubular member is cyclically closed by said inner tubular member at a predetermined angular position of said inner tubular member and wherein, at such angular position, said channel is in enhanced communication with said source of aspiration. from an aspiration-only operating mode to an operating mode incorporating irrigation by communicating fluid from a fluid source to the shaver blade assembly, said shaver blade assembly having a fluid inlet, in an outer tubular member said adapter comprising:

an annular housing adapted to selectively receive said shaver blade assembly;

means for releasably securing said annular housing contiguously adjacent said fluid inlet;

an inlet port means for communicating fluid from said fluid source to said fluid inlet.

5. A shaver blade assembly according to claim 1 wherein said elongated channel comprises a recess formed in the inner surface of said outer tubular member.

6. A shaver blade assembly according to claim 5 wherein said cutting opening at said distal end of said outer tubular member is cyclically closed by said inner tubular member at a predetermined angular position of said inner tubular member and wherein, at such angular position, said channel is in communication with said irrigating fluid inflow port.

7. A shaver blade assembly according to claim 1 wherein said elongated channel comprises a recess formed in the outer surface of said inner tubular member.

8. A shaver blade assembly according to claim 6 wherein said elongated channel comprises a flat formed in the outer surface of said inner tubular member.

9. A shaver blade assembly according to claim 1 wherein the distal ends of said inner and outer tubular members are angled so that the axes of their distal ends extend at a predetermined angle to the axes of their proximal ends.

10. A shaver blade assembly according to claim 1 wherein said fluid adapter means comprises:

an annular housing adapted to receive said shaver blade assembly;

means for securing said annular housing to said shaver blade assembly; and an inlet port means for communicating fluid from said source of fluid to said irrigating fluid inflow port.

11. A shaver blade assembly according to claim 10 wherein said fluid adapter means further comprises comprises means for securing said adapter in a predetermined angular position relative to said irrigating fluid inflow port.

12. A shaver blade assembly according to claim 10 wherein said fluid adaptor means further comprises integral proximal and distal seal means situated proximally and distally, respectively, of said inlet port means.

13. A shaver blade assembly according to claim 12 wherein said proximal seal means further comprises a radially inwardly extending annular lip and wherein said distal seal means further comprises a frustoconical annular surface having a predetermined radius of curvature and adapted to seat against a predetermined portion of said hub of said outer tubular member.

14. A shaver blade assembly according to claim 1 wherein said fluid adapter means comprises fluid seals to minimize leakage between said adapter and said surface of said outer tubular member.

15. A shaver blade assembly according to claim 1 further comprising means for detachably securing said fluid adapter means distally of said hub at said proximal end of said outer tubular member.

16. A shaver blade assembly according to claim 1 wherein said outer tubular member further comprises a tubular cylindrical body extending distally from said hub and wherein said irrigating fluid inflow port comprises an aperture in said cylindrical body, distal to said hub.

17. An irrigating adapter for converting a shaver blade assembly from an aspiration-only operating mode to an operating mode incorporating irrigation by communicating fluid from a fluid source to the shaver blade assembly, said shaver blade assembly having a fluid inlet, in an outer tubular member said adapter comprising:

an annular housing adapted to selectively receive said shaver blade assembly;

means for releasably securing said annular housing contiguously adjacent said fluid inlet;

an inlet port menas for communicating fluid from said fluid source to said fluid inlet.

18. An adapter according to claim 17 further comprising:
an annular fluid channel within said housing adapted to be juxtaposed adjacent said fluid inlet when said adapter is secured to said shaver blade assembly.

19. An irrigating adapter according to claim 17 further comprising integral proximal and distal seal means situated proximally and distally, respectively, of said inlet port means.

20. An irrigating adapter according to claim 19 wherein said proximal seal means further comprises a radially inwardly extending annular lip and wherein said distal seal means further comprises a frustoconical annular surface having a predetermined radius of curvature and adapted to seat against a predetermined portion of said hub of said outer tubular member.

21. An irrigating adapter according to claim 17 wherein said shaver blade assembly has an elongated inner tubular member movable within an elongated outer tubular member and wherein said fluid inlet comprises an aperture in said outer tubular member.

22. A method for using a shaver blade assembly with a source of fluid, said shaver blade assembly having an elongated inner tubular member movable relative to an elongated outer tubular member, comprising the steps of:

providing a fluid inlet port in the wall of said outer tubular member;

providing a fluid adapter means for connecting said port to a source of fluid and communicating fluid thereto;

selectively attaching said fluid adapter means to said shaver blade assembly and said source of fluid when irrigating fluid is desired at a surgical site;

operating said shaver blade assembly while it is in operative communication with said source of fluid.

23. A method of adapting a shaver blade assembly having an elongated inner tubular member cyclically movable within a stationary elongated outer tubular member for use at a surgical site in a mode selected from the group of modes comprising an aspiration-only mode, an irrigation-only mode and an irrigating/aspirating mode comprising the steps of:

forming a fluid inlet port in the wall of said outer tubular member;

providing a fluid source;

providing a fluid adapter means selectively engageable adjacent said port and with said fluid source for communicating fluid to said port;

selectively connecting said fluid adapter means to said port and said source of fluid to communicate fluid to said port when operation of said shaver blade assembly in an irrigation-only mode or an irrigating/aspirating mode is desired;

providing an aspiration source and connection means for connecting said shaver blade assembly to said aspiration source;

selectively connecting said aspiration source to said shaver blade assembly when operation of said shaver blade assembly in an irrigating/aspirating mode or an aspiration-only mode is desired.

24. A method of forming a shaver blade assembly having an elongated inner tubular member cyclically movable within a stationary elongated outer tubular member in order to make the shaver blade assembly capable of use in an irrigation-only mode, an aspiration-only mode and an aspiration/irrigation mode, comprising the steps of:

providing a fluid port in the outer tubular member;

providing a longitudinally extending channel between said inner and outer tubular members.

25. A method according to claim 24 wherein said longitudinally extending channel comprises an elongated recess in the inner surface of said outer tubular member in communication with said fluid port, said elongated recess terminating a predetermined distance from the distal tip of the outer member; further comprising:

said inner member extending distally beyond said elongated recess; and an arcuate recess formed in the outer surface of said inner member, said arcuate recess extending longitudinally a predetermined distance in order to cyclically be in communication with the distal end of said elongated recess when said arcuate recess is angularly aligned with said longitudinally extending channel.

26. A method according to claim 24 wherein the interior of said outer tubular member has a tear-drop cross-section such that a predetermined arcuate portion of the wall of said outer tubular member extends radially outwardly a greater distance than adjacent wall portions in order to create a channel between said inner and outer members; further comprising:

a distal tip means having a tear-drop cross-section at its proximal end for being mateably secured to the distal end of said outer tubular member, said distal tip means having an inner circular bore adapted to rotatably receive the distal end of said inner tubular member, a communicating channel means enabling communication between said elongated channel and the interior of said inner tubular member.

27. A method according to claim 24 wherein said outer tubular member comprises a hollow cylindrical body surrounding said inner tubular member, and wherein said step of providing a fluid port further comprises the step of forming an aperture in said hollow cylindrical body, said aperture for communicating with said longitudinally extending channel.

28. A conversion kit comprising:

a shaver blade assembly comprising an elongated outer tubular member having a distal end, a proximal end, a cutting opening at said distal end, a hub at said proximal end, and an irrigating fluid inflow port in said outer tubular member intermediate said distal and proximal ends;

an elongated inner tubular member adapted to move relative to said outer tubular member and having a distal end, proximal end, a cutting window at said distal end, and a hub at said proximal end:

an elongated channel between said irrigating fluid inflow port and said cutting window, said channel defined by the inner surface of said outer member and the outer surface of said inner member and adapted to operate in an irrigation-only mode, an aspiration-only mode and an irrigation/aspiration mode;

an adapter means for converting said shaver blade assembly to operate in one of said modes, said shaver blade assembly automatically set to operate in an aspiration-only mode when said adapter is not in communication with a source of irrigation.

* * * * *